United States Patent
Zumbrum et al.

(10) Patent No.: US 12,044,335 B2
(45) Date of Patent: Jul. 23, 2024

(54) PINCH CLAMP FOR FLEXIBLE CONDUITS

(71) Applicant: Sartorius Stedim North America Inc., Bohemia, NY (US)

(72) Inventors: Michael Zumbrum, New Oxford, PA (US); William Kimmick, Mechanicsburg, PA (US)

(73) Assignee: Sartorius Stedim North America Inc., Bohemia, NY (US)

( * ) Notice: Subject to any disclaimer, the term of this patent is extended or adjusted under 35 U.S.C. 154(b) by 0 days.

(21) Appl. No.: 17/790,017

(22) PCT Filed: Dec. 8, 2021

(86) PCT No.: PCT/US2021/062299
§ 371 (c)(1),
(2) Date: Jun. 29, 2022

(87) PCT Pub. No.: WO2022/125602
PCT Pub. Date: Jun. 16, 2022

(65) Prior Publication Data
US 2023/0349472 A1    Nov. 2, 2023

Related U.S. Application Data

(60) Provisional application No. 63/122,614, filed on Dec. 8, 2020.

(51) Int. Cl.
*F16K 7/06* (2006.01)
*A61M 39/28* (2006.01)

(52) U.S. Cl.
CPC .............. *F16K 7/06* (2013.01); *A61M 39/28* (2013.01); *A61M 39/286* (2013.01)

(58) Field of Classification Search
CPC ..... F16K 7/06; A61M 39/281; A61M 39/287; A61M 39/28; A61M 39/286
(Continued)

(56) References Cited

U.S. PATENT DOCUMENTS

| 3,042,067 A | * 7/1962 | Hidding .............. A61M 39/283 251/8 |
| 4,262,711 A | 4/1981 | Anderson |

(Continued)

FOREIGN PATENT DOCUMENTS

| CA | 2320395 A1 | 3/2002 |
| EP | 2089082 B1 | 5/2015 |

(Continued)

OTHER PUBLICATIONS

International Search Report for PCT/US2021/062299 issued Mar. 10, 2022.

(Continued)

*Primary Examiner* — John Bastianelli

(74) *Attorney, Agent, or Firm* — Womble Bond Dickinson (US) LLP

(57) ABSTRACT

A clamp for closing a flexible tube includes an anvil and a hammer. The anvil includes a passage and a slot defined therein. The passage is configured to receive a flexible tube therethrough. The hammer is slidably received within the slot of the anvil. The hammer is securable in a first position in which the passage of the anvil is substantially unoccluded and a second position in which the passage of the anvil is occluded. The hammer and the anvil are configured to prevent fluid from flowing through the flexible tube received in the passage when the hammer is in the closed position. The hammer is substantially within the anvil in the closed position.

12 Claims, 7 Drawing Sheets

(58) Field of Classification Search
USPC .............................................. 251/7; 604/250
See application file for complete search history.

(56) References Cited

U.S. PATENT DOCUMENTS

| | | | | |
|---|---|---|---|---|
| 4,616,802 | A | * | 10/1986 | Tseng .................... A61M 39/28 251/7 |
| 4,643,389 | A | | 2/1987 | Elson et al. |
| 4,960,259 | A | * | 10/1990 | Sunnanvader ........ A61M 39/28 251/7 |
| 6,287,281 | B1 | * | 9/2001 | Nishtala ................ A61M 25/02 604/178 |
| 6,676,253 | B2 | | 1/2004 | Hsu et al. |
| 8,267,370 | B2 | | 9/2012 | Fisher et al. |
| 8,474,784 | B2 | * | 7/2013 | Kashmirian ........ A61M 39/284 251/10 |
| 8,863,364 | B2 | * | 10/2014 | Gay .................... A61M 39/146 29/524.1 |
| 9,060,920 | B2 | * | 6/2015 | Hirabuki ............... A61J 1/2089 |
| 10,195,418 | B2 | | 2/2019 | Newell et al. |
| 2010/0106101 | A1 | | 4/2010 | Fisher et al. |
| 2016/0067538 | A1 | | 3/2016 | Friedberg et al. |
| 2017/0232247 | A1 | * | 8/2017 | Sonderegger ......... A61M 39/28 604/250 |
| 2019/0015565 | A1 | | 1/2019 | Myers et al. |
| 2020/0398041 | A1 | | 12/2020 | Mermet |

FOREIGN PATENT DOCUMENTS

| | | |
|---|---|---|
| EP | 2583716 B1 | 7/2015 |
| ES | 2222118 T3 | 2/2005 |
| GB | 1025947 A | 4/1966 |
| WO | 2014162376 A1 | 10/2014 |
| WO | 2022125602 A1 | 6/2022 |

OTHER PUBLICATIONS

International Preliminary Report on Patentability for PCT Application PCT/US2021/06229 issued Jun. 13, 2023, 9 pages.

* cited by examiner

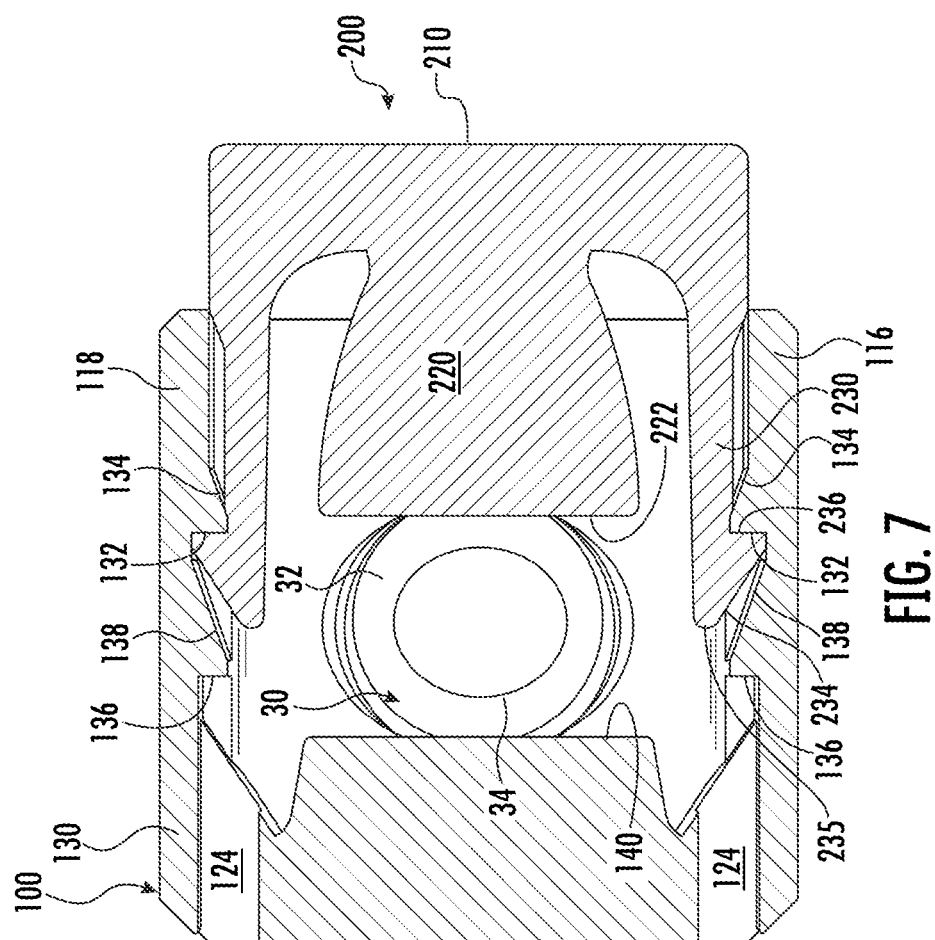
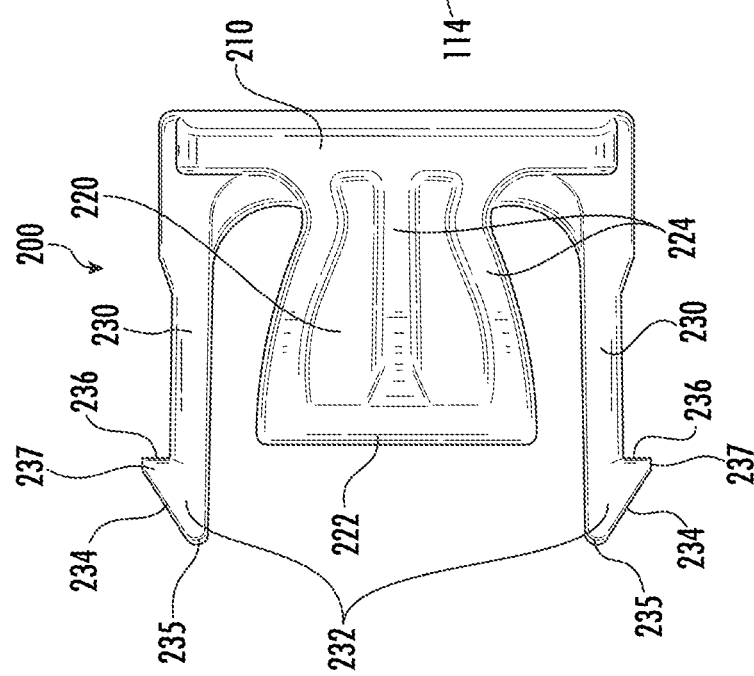
FIG. 7
FIG. 6

PINCH CLAMP FOR FLEXIBLE CONDUITS

BACKGROUND

1. Technical Field

The present disclosure relates to fluid transfer assemblies, and more specifically, clamps for aseptic fluid transfer assemblies.

2. Discussion of Related Art

Biopharmaceutical and pharmaceutical drug developers and manufactures often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the fluids through conduits for purposes of sampling, packaging, mixing, separating, or passing between stations for various steps of the manufacturing process.

The manufacturing and testing processes required by biopharmaceutical and pharmaceutical companies require significant opportunities for fluid transfer. Often, several fluid pathways are required to enter or exit various containers. It may be necessary to stop or terminate the flow of fluid through one or more of the fluid pathways. In some applications, pinch clamps have been used to temporarily or permanently terminate fluid through a fluid pathway. Such pinch clamps may break or open unintentionally when bumped or jostled while being moved or transported. In addition, pinch clamps may extend along a substantial length of the fluid pathway being clamped.

SUMMARY

In some applications, the space between fluid pathways is limited such that traditional pinch clamps are difficult or impossible to use on the fluid pathways. Accordingly, there is a continuing need for clamps that allow for permanent or temporary termination of flow through a fluid pathway. Additionally, there is a continuing need for clamps that prevent unintended separation or opening.

In an embodiment of the present disclosure, a clamp for closing a flexible tube includes an anvil and a hammer. The anvil includes a passage and a slot defined therein. The passage is configured to receive a flexible tube therethrough. The hammer slidably received within the slot of the anvil. The hammer is securable in a first position in which the passage of the anvil is substantially unoccluded and a second position in which the passage of the anvil is occluded. The hammer and the anvil are configured to prevent fluid from flowing through a flexible tube received in the passage when the hammer is in the second position. The hammer is disposed substantially within the anvil in the second position.

In embodiments, the hammer includes pair of arms and a head positioned between the pair of arms. Each arm may have a finger. The anvil may include a first rack and a second rack that opposes the first rack. The first rack and the second rack may each define a portion of the slot. The first rack may include a first detent and a second detent. The finger of one of the first or second arms may be receivable in the first and second detents. The hammer may be in the first position when the finger is received in the first detent and in the second position when the finger is received in the second detent.

In some embodiments, the anvil includes a cutout defined adjacent the second detent. The cutout may provide access to the finger such that the finger is capable of being released from the second detent by a digit of a user. The anvil and the hammer may be configured to function when cryogenically frozen.

In another embodiment of the present disclosure, a clamp includes an anvil and a hammer. The anvil includes a passage and a slot defined therein. The passage and the slot are orthogonal to one another with the passage being configured to receive a flexible tube therethrough. The hammer is slidably received within the slot. The hammer has a pair of arms and a head positioned between the pair of arms. The hammer has a first position in which the head is disposed outside of the passage and a second position in which the head is disposed within the passage. The head is configured to cooperate with the anvil to prevent a fluid from flowing through the flexible tube in the second position.

In embodiments, the anvil includes a rack that is defined in an interior wall thereof. One of the pair of arms may be configured to ratchet along the rack to secure the hammer in the first position and the second position. The anvil may include a notch defined adjacent the rack. The notch may be configured to expose a portion of the hammer when the hammer is in the second position such that the hammer is capable of being released form the second position by one or more digits of a user.

In another embodiment of the present disclosure, a method of closing a flexible tube includes positioning a clamp with a flexible tube disposed within a passage of an anvil of the clamp and advancing a hammer of the clamp within a slot of the anvil to a closed position in which the hammer cooperates with the anvil to pinch walls of the flexible tube together to prevent fluid flow through a lumen of the flexible tube.

In embodiments, positioning the clamp includes sliding the clamp over an end of the flexible tube. Positioning the clamp may include the hammer being in an open position within the slot of the anvil in which fluid flow through the lumen is allowed.

In some embodiments, advancing the hammer within the slot may include inserting the hammer into the slot when the anvil is positioned on the flexible tube. Advancing the hammer within the slot may include pressing a back of the hammer into the anvil until the back of the hammer is flush with a sidewall of the anvil.

In certain embodiments, advancing the hammer within the slot includes sliding the hammer from an open position in which flow is permitted through the lumen of the flexible tube to the closed position. Sliding the hammer may include ratcheting an arm of the hammer over a rack of the anvil from the open position to the closed position.

In particular embodiments, advancing the hammer includes a head of the hammer cooperating with a stop wall of the anvil to pinch the flexible tube between the head and the stop wall. The method may include releasing the hammer from the closed position such that the hammer retracts from the closed position to an open position in which fluid is allowed to flow through the flexible tube.

In embodiments, releasing the hammer may include pressing two fingers of the hammer inward to release the hammer. Pressing two fingers of the hammer inward may include engaging the fingers of the hammer with digits of a user. The method may include freezing the flexible tube and the clamp with the clamp remaining in the closed position. Freezing the flexible tube and the clamp may include freezing the clamp and the flexible tube to cryogenic temperatures.

Further, to the extent consistent, any of the embodiments or aspects described herein may be used in conjunction with any or all of the other embodiments or aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 6 is a top view of the hammer of FIG. 3;

FIG. 7 is a cross-sectional view of the clamp and tube of FIG. 1 taken along the section line 7-7 of FIG. 1;

DETAILED DESCRIPTION

Figure 2:
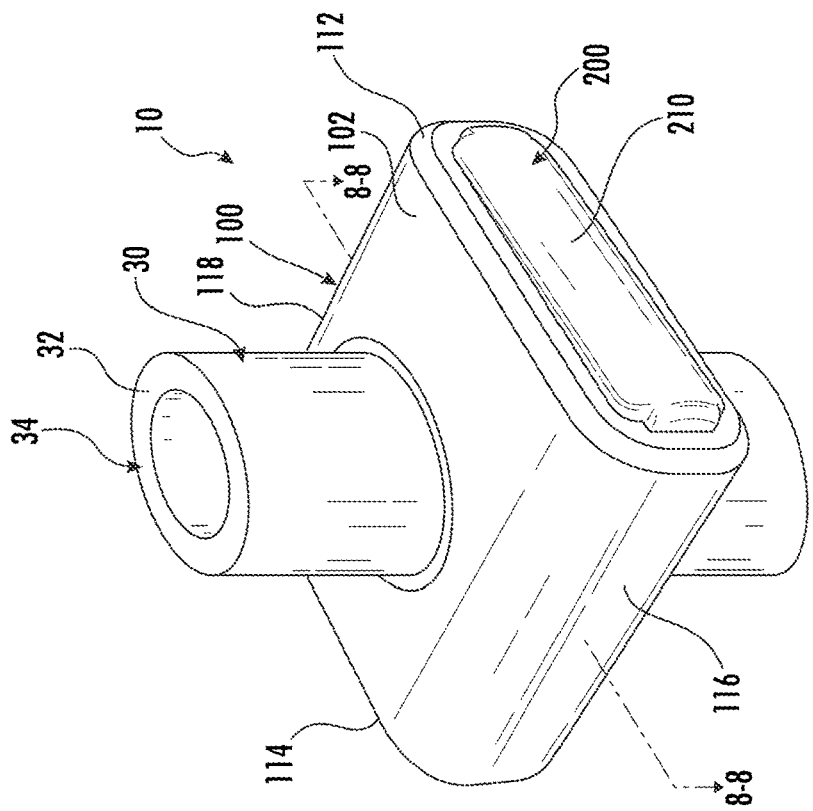
FIG. 2 is a perspective view of the clamp of FIG. 2 in a closed position.

The present disclosure will now be described more fully hereinafter with reference to example embodiments thereof with reference to the drawings in which like reference numerals designate identical or corresponding elements in each of the several views. These example embodiments are described so that this disclosure will be thorough and complete, and will fully convey the scope of the disclosure to those skilled in the art. Features from one embodiment or aspect can be combined with features from any other embodiment or aspect in any appropriate combination. For example, any individual or collective features of method aspects or embodiments can be applied to apparatus, product, or component aspects or embodiments and vice versa. The disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

Figure 1:
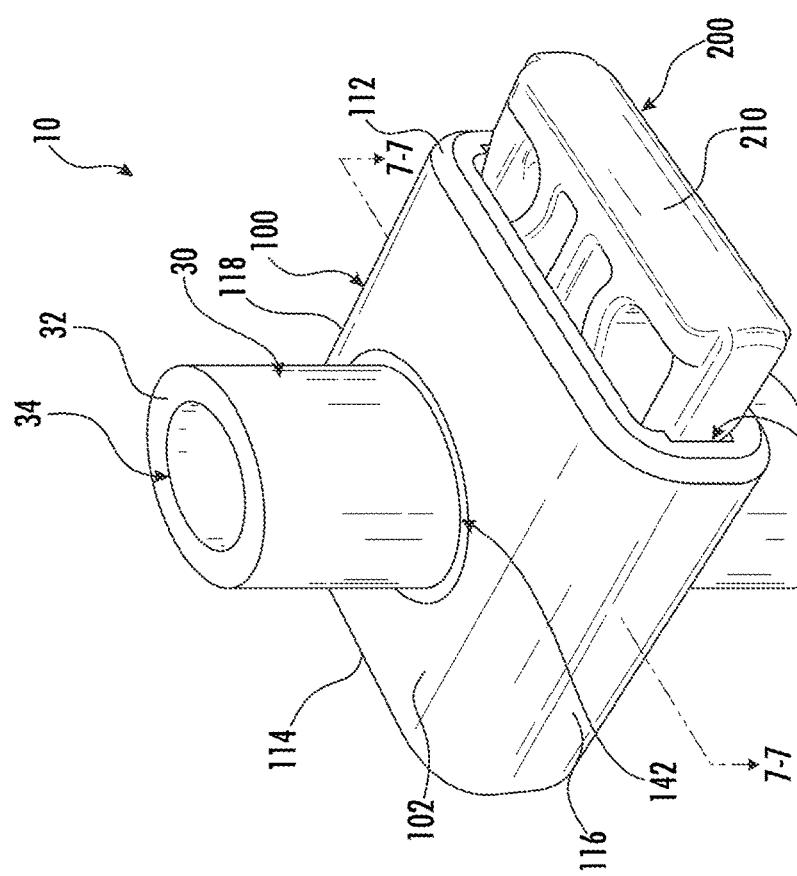
FIG. 1 is a perspective view of a clamp provided in accordance with an embodiment of the present disclosure in an open position with a flexible tube received within a passage of the clamp.
Figure 3:
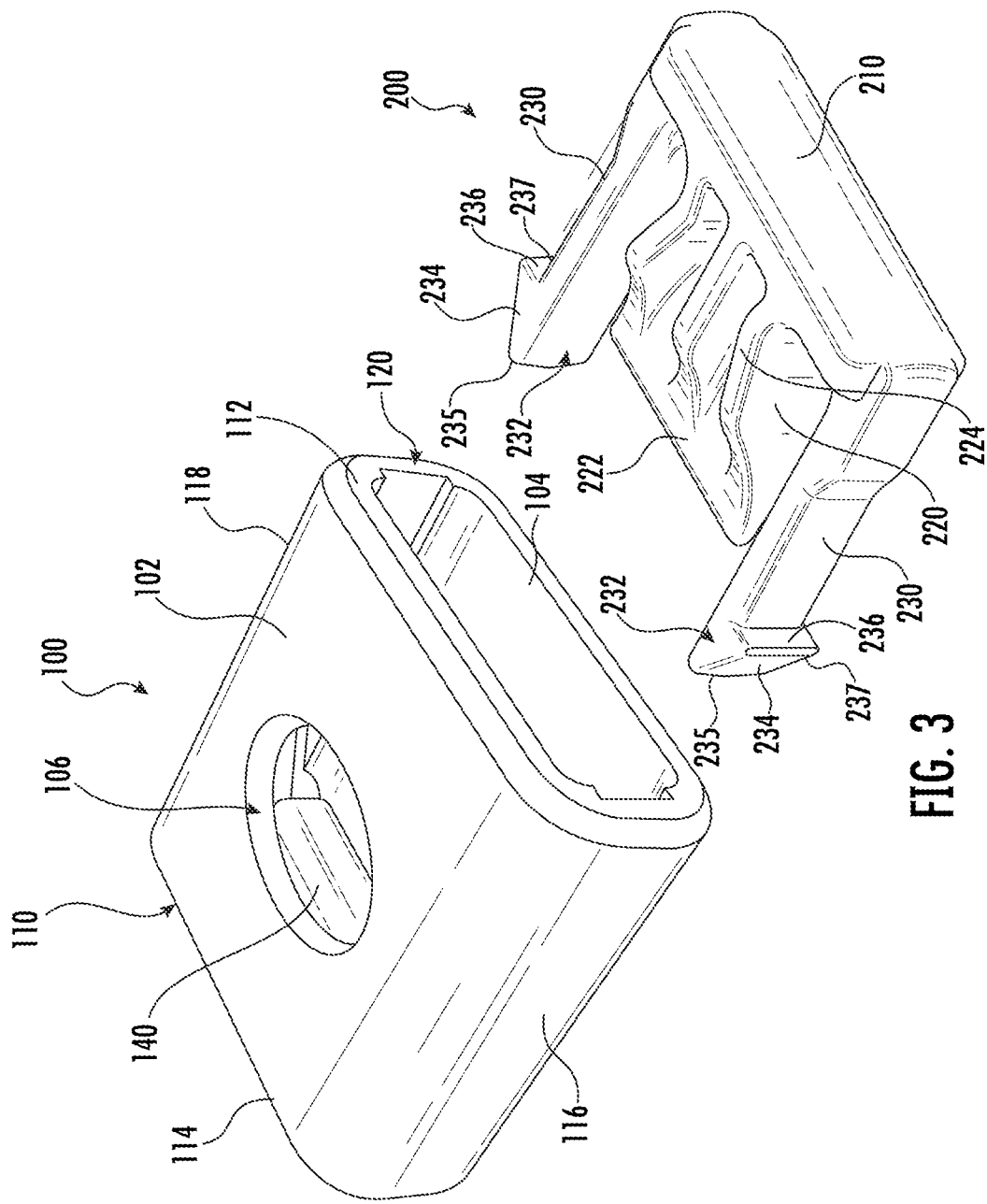
FIG. 3 is a perspective view of the clamp of FIG. 1 with an anvil separated from a hammer of the clamp.

Referring now to FIGS. 1-3, a pinch clamp 10 is provided in accordance with an embodiment of the present disclosure. The pinch clamp 10 includes an anvil 100 and a hammer 200 that is translatable within a slot 120 defined within the anvil 100. The anvil 100 also defines a passage 106 that passes transversely through the anvil 100 that is sized and dimensioned to receive a conduit or tube 30 therethrough. The tube 30 has flexible walls 32 that define a lumen 34 of the tube 30 for the flow of fluid through the tube 30.

As shown in FIG. 1, the clamp 10 has a first or open position in which the hammer 200 is disposed outside of or substantially outside of the slot 120 of the anvil 100. In the open position of the clamp 10, the tube 30 is uncompressed or substantially uncompressed by the clamp 10 such that the lumen 34 of the tube 30 is open to allow fluid to flow through the lumen 34. As shown in FIG. 2, the clamp 10 also has a second or closed position in which the hammer 200 is disposed within the slot 120 of the anvil 100 such that the tube 30 is compressed between the anvil 100 and the hammer 200. Specifically, the hammer 200 compresses the flexible walls 32 of the tube 30 together such that the lumen 34 of the tube 30 is closed to prevent fluid flow through the lumen 34. As described in greater detail below, in the closed position, the hammer 200 is retained in the slot 120 of the anvil 100 such that the clamp 10 is locked in the closed position or prevented from retracting to the open position. In the closed position, the hammer 200 may be substantially within the slot 120 of the anvil 100 such that only a back 210 of the hammer 200 protrudes from the slot 120.

Referring to FIG. 3, the anvil 100 has a body 110 which is substantially in the shape of a rectangular prism. The sides of the body 110 may be substantially equal in length such that the body 110 has a square cross-section when taken along a transverse axis or the sides of the body 110 may have unequal lengths. The profile or thickness of the body 110 along the transverse axis is less than the length of the sides of the body 110. The thickness of the body 100 may be minimized to reduce the thickness of the clamp 10.

The body 110 includes a top wall 102 and a bottom wall 104 such that the thickness of the body 110 is defined between the top and bottom walls 102, 104. The top and bottom walls 102, 104 each include an opening 106 that are axially aligned with one another to define the passage 142 (FIG. 5) through the body 110. The openings 106 may be circular or substantially circular. For example, the openings 106 may be slightly oval or elliptical in shape, as best shown in FIG. 7.

Figure 5:
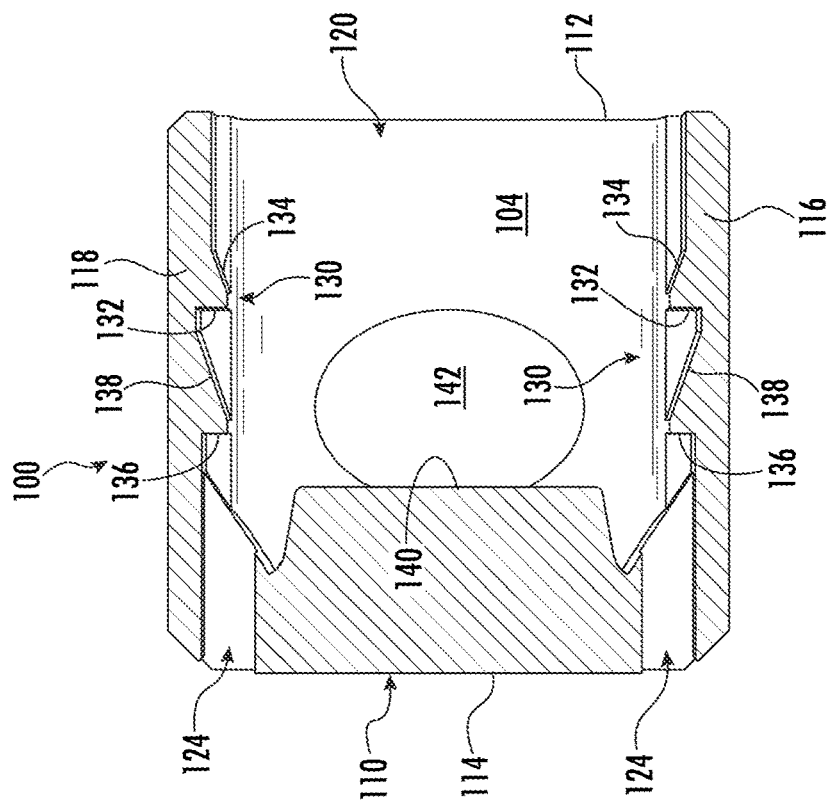
FIG. 5 is a cross-sectional view of the anvil taken along the section line 5-5 of FIG. 4.
Figure 4:
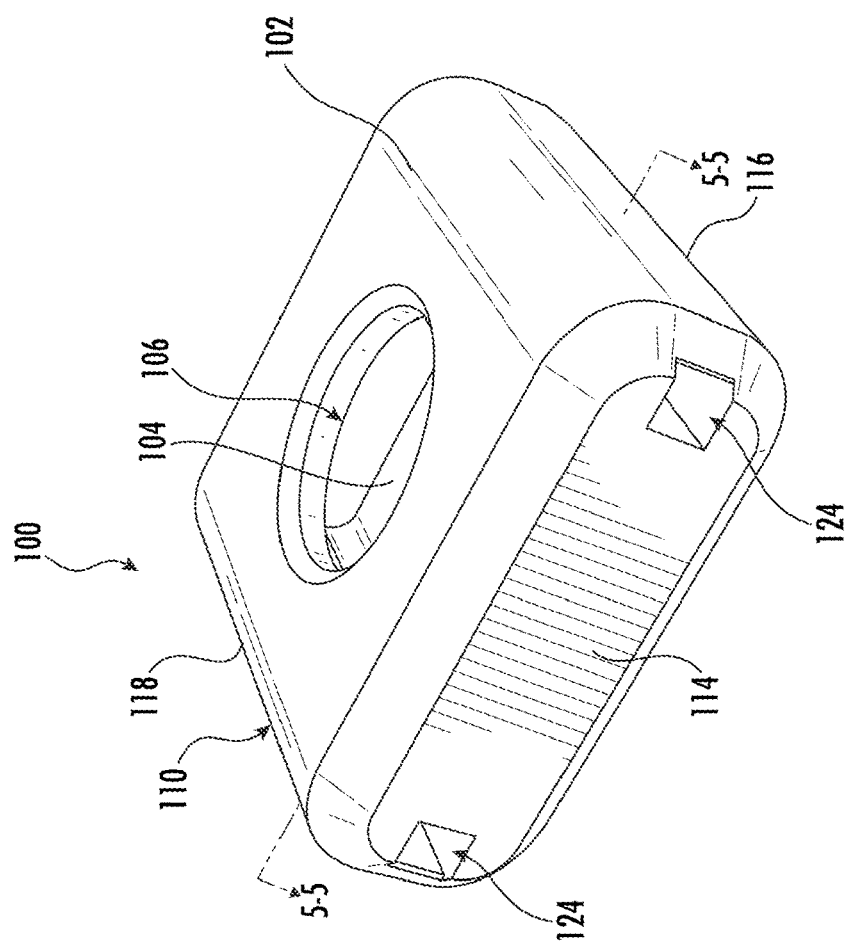
FIG. 4 is rear perspective view of the anvil of the clamp of FIG. 1.

With reference to FIGS. 4 and 5, the body 110 includes a first sidewall 112, a second sidewall 114, a third sidewall 116, and a fourth sidewall 118. The second sidewall 114 is opposite the first sidewall 112 and the fourth sidewall 118 is opposite the third sidewall 116. The first sidewall 112 and the second sidewall 114 each intersect the third and fourth sidewalls 116, 118. The slot 120 passes through the first sidewall 112 of the body 110 towards the second sidewall 114 of the body 110 and terminates at a stop wall 140 of the anvil 100. The stop wall 140 extends in a direction substantially parallel to the first and second sidewalls 112, 114 and perpendicular to the third and fourth walls 116, 118. As detailed below, the stop wall 140 is configured to oppose a portion of the hammer 200 to compress the tube 30 therebetween. The slot 120 may include sleeves 124 that each extend past edges of the stop wall 140 and through the second sidewall 114 of the body 110.

The inside surface of the third sidewall 116 and/or the fourth sidewall 118 includes a rack 130 having a first or open detent 132 and a second or closed detent 136 defined therein. The open detent 132 is disposed between the closed detent 136 and the first sidewall 112. The rack 130 may include a first ramp 134 adjacent the open detent 132 that is positioned between the open detent 132 and the first sidewall 112 and extends towards the opposite sidewall as the first ramp 134 extends in a direction from the first sidewall 112 towards the second sidewall 114. Additionally or alternatively, the rack 130 may include a second ramp 138 that is positioned between the closed detent 136 and the open detent 132 and extends towards the opposite sidewall as the second ramp 138 extends in a direction from the first sidewall 112 towards the second sidewall 114. The second ramp 138 may be linear between the open detent 132 and the closed detent 136.

Referring to FIG. 6, the hammer 200 includes a back 210, a head 220, and a pair of arms 230. The back 210 is sized and dimensioned to pass through the slot 120 defined in the first sidewall 112 of the anvil 100. The head 220 extends from the back 210 between the arms 230 to a face wall 222 of the head 220. The face wall 222 is configured to engage the tube 30 to compress the tube 30 between the face wall 222 and the stop wall 140 when the hammer 200 is in the closed position (FIG. 2). The head 220 may include ribs 224 that extend from the back 210 to the face wall 222 to strengthen or provide rigidity to the head 220 to prevent the head 220 from deflecting towards the top or bottom wall 102, 104 when disposed within the slot 120. Additionally or alternatively, the ribs 224 may engage the top or bottom wall 102, 104 to position, guide, or align the hammer 200 within the slot 120. The ribs 224 may slope away from a centerline of the head 220 as the ribs 224 extend from the face wall 222 towards the back 210, e.g., towards the top and bottom walls 102, 104 when received in the slot 120. The ribs 224 may reinforce the head 220 while minimizing an amount of material of the head 220.

The arms 230 extend from the back 210 in the same direction as the head 220 such that the head 220 is disposed between the arms 230. Each arm 230 includes a finger 232 that selectively engages the rack 130 of the third or fourth sidewall 116, 118. Specifically, the finger 232 includes a leading surface 234 and a lock surface 236 that engage the rack 130. The leading surface 234 is angled such that as the leading surface 234 extends away from the back 210, the leading surface 234 extends inward towards the other arm 230. The leading surface 234 may form a leading edge 235 at the end of the finger 232. The leading edge 235 may be sharp or may be blunted, e.g., rounded. The leading surfaces 234 may be angled to work in concert with the ramps 134, 138 of the rack 130. The lock surface 236 extends inward from a trailing edge 237 of the leading surface 234 surface opposite the leading edge 235 of the arm 232 towards the other arm 232 to form a surface substantially parallel with the back 210. The lock surface 236 may be configured to be substantially parallel to the first and second sidewalls 112, 114 of the anvil 100 when the hammer 200 is received within the slot 120. The lock surface 236 is configured to interact with the detents 132, 136 to prevent the hammer 200 from backing out or retracting out of the slot 120, e.g., moving in a direction towards the first sidewall 112. In some embodiments, the arms 230 may be engaged to compress the fingers 232 towards one another such that the hammer 200 is removable from the slot 120 after being in the open position.

Figure 8:
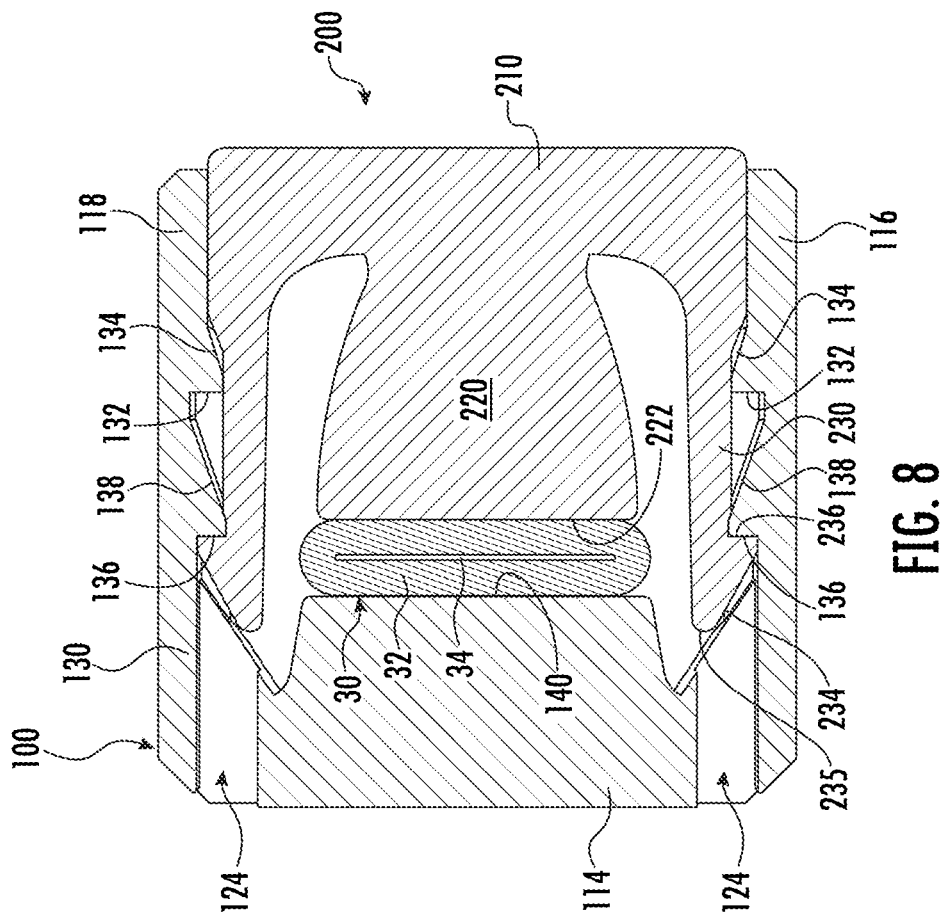
FIG. 8 is a cross-sectional view of the clamp and the tube of FIG. 2 taken along the section line 8-8 of FIG. 2.

With reference to FIGS. 7 and 8, the clamp 10 is used to clamp or secure the tube 30 in a closed position such that fluid is prevented from flowing through the lumen 34 of the tube 30. The body 110 of the anvil 100 is positioned over the tube 30 such that the tube 30 is within the passage 142 (FIG. 1) of the anvil 100, e.g., the tube 30 passes through the openings 106 (FIG. 3) in the top and bottom walls 102, 104 of the body 110. The anvil 100 may be positioned over the tube 30 such that the lumen 34 of the tube 30 is substantially open or unoccluded. When the tube 30 is substantially open, fluid may flow through the lumen 34 of the tube 30. In some embodiments, the stop wall 140 of the anvil 100 may engage the wall 32 of the tube 30 to prevent the anvil 100 from freely sliding longitudinally along the tube 30 without occluding or affecting flow through the tube 30. For example, the stop wall 140 may frictionally engage the wall 32 of the tube 30 such that the anvil 100 can be slid longitudinally along the tube 30 but maintains a stable location along the tube 30, e.g., the anvil 100 maintains a position along the tube 30 absent a force being applied to the anvil 100 to slide the anvil 100 along the tube 30. The engagement between the stop wall 140 and the wall 32 of the tube 30 may slightly deform the wall 32 of the tube 30. In particular embodiments, one or both of the openings 106 are slightly smaller than an outer diameter of the tube 30 such that the wall 32 of the tube 30 frictionally engages the top and/or bottom walls 102, 104 to position the anvil 100 at a stable location along the tube 30.

With the anvil 100 positioned over the tube 30, the hammer 200 may be inserted into the slot 120 of the anvil 100 and secured in the open position as shown in FIG. 7. To insert the hammer 200 into the slot 120, the arms 230 are inserted into the slot 120 with the leading surface 234 of each of the arms 230 engaging the racks 130 of the third and fourth sidewalls 116, 118. The engagement of the leading surfaces 234 may laterally align or position the hammer 200 within the slot 120 of the anvil 100. Additionally, the engagement of the rib 224 (FIG. 6) with the top or bottom walls 102, 104 (FIG. 3) may guide or vertically align the hammer 200 within the slot 120.

The hammer 200 is inserted or advanced in the slot 120 by pressing the back 210 of the hammer 200 towards the stop wall 140 or the second sidewall 114 of the anvil 100. As the hammer 200 is inserted into the slot 120, the leading surfaces 234 of the arms 230 engage or ratchet over the first ramp 134 and are received in the open detents 132. The engagement of the leading surfaces 234 with the first ramp 134 deflect the arms 230 inward. When the trailing edge 237 of the leading surfaces 234 (FIG. 6) is beyond the first ramp 134, the arm 230 return to a substantially straight configuration such that the leading surfaces 234 engage the second ramp 138 and the lock surfaces 236 are received in the open detents 132. The arms 230 may be returned to the substantially straight configuration as a result of self-biasing of the arms 230 to the substantially straight configuration. The self-biasing of the arms 230 may be provided by the material properties, e.g., elasticity, of the material forming the arms 230.

As a result of the self-biasing of the arms 230 urging the leading surfaces 234 into the second ramps 138, the engagement of the leading surfaces 234 and the second ramps 138 may urge the hammer 200 out of the slot 120, e.g., in a direction from the second sidewall 114 towards the first sidewall 112, until the stop surfaces 236 engage the open detent 136 to prevent the hammer 200 from backing out of the slot 120 such that the hammer 200 is secured or maintained in the open position. In the open position, the face wall 222 of the hammer 200 may engage the wall 32 of the tube 30. In the open position, engagement of the face wall 222 with the wall 32 does not occlude the lumen 34 of the tube 30. In certain embodiments, the hammer 200 may be in the open position when the anvil 100 is positioned over the tube 30. In the open position, the self-biasing of the arms 230 and/or the engagement of the face wall 222 with the wall 32 of the tube 30 may provide a rattle-free performance of the hammer 200. The rattle-free performance of the hammer 200 may prevent or reduce generation of particulates to prevent particulates from becoming part of the fluid stream and eventually being part of the product within a downstream vessel. Some authorities may have strict requirements for particulate concentrate within a product, e.g., a drug product.

With the hammer 200 in the open position, flow of fluid through the lumen 34 of the tube 30 is permitted. The tube 30 may be used for a plurality of uses including, but not limited to, transferring fluid from one vessel to another, sampling fluid from a vessel, venting a vessel, distributing fluid from a large vessel to one or more smaller vessels, or collecting fluids from small vessels into a single large vessel. In some embodiments, one end of the tube 30 may be bonded to a vessel, a vessel cap, or a vessel closure. In certain embodiments, one end of the tube 30 may be unrestrained. The unrestrained end of the tube 30 may include a luer connection, a septum, a filter vent, or another closure to selectively close the unrestrained end of the tube 30 or to connect the unrestrained end of the tube 30 to another tube or vessel. In particular embodiments, both ends of the tube 30 may be unrestrained or both ends of the tube 30 may be secured to a vessel, vessel cap, or vessel closure.

When flow of fluid through the lumen 34 of the tube 30 is undesired, either before flow of fluid through the lumen 34 or after flow of fluid through the lumen 34, the hammer 200 may be transitioned to the closed position such that the lumen 34 is closed or fully occluded to prevent the flow of fluid through the lumen 34 of the tube 30, as shown in FIG. 8. To transition the hammer 200 from the open position to the closed position, the back 210 of the hammer 200 is pressed into the slot 120, e.g., in a direction from the first sidewall 112 towards the second sidewall 114. As the back 210 is pressed or advanced into the slot 120, the leading surfaces 234 of the arms 230 engage the second ramps 138 to deflect the arms 230 inward, e.g., towards one another, until the trailing end 237 (FIG. 6) is beyond the second ramp 138 and in the closed detent 136. When the trailing end 237 is in the closed detent 136, the stop surface 236 may engage the closed detent 136 to prevent the hammer 200 from backing out of the anvil 100. As the hammer 200 is pushed in or advanced into the anvil 100, the face wall 222 of the hammer 200 engages wall 32 of the tube 30 to compress the tube 30 between the face wall 222 and the stop wall 140. When the hammer 200 is in the closed position, the walls 32 of the tube 30 may contact one another and the tube 30 may be deformed to be substantially flat such that the lumen 34 is pinched closed or fully occluded to prevent the flow of fluid through the tube 30. The walls 32 of the tube 30 may apply a force urging the hammer 200 and the anvil 100 towards the open position which is resisted by the engagement of the stop surfaces 236 with the closed detents 136. In the closed position, the clamp 10 may prevent flow through the tube 30 in a variety of environmental conditions such that a vessel in fluid communication with the tube 30 is maintained in an aseptic condition. For example, the vessel, tube 30, and clamp 10 may be frozen with the clamp 10 maintaining an aseptic closure of the tube 30. In certain embodiments, the vessel, tube 30, and the clamp 10 may be cryogenically frozen with the clamp 10 maintaining an aseptic closure of the tube 30. Cryogenically frozen may include being maintained at a temperature in a range of −60 degrees C. to −190 degrees C., more specifically in a range of −70 degrees C. to −100 degrees C. In addition, the clamp 10 may be subjected to elevated temperatures with the clamp 10 maintaining an aseptic closure of the tube 30. For example, the clamp 10 may be autoclaved or subjected to steam sterilization in a range of 121 degrees C. to 150 degrees C. As such the pinch clamp 10 may maintain an aseptic closure of the tube 30 in a temperature range of −190 degrees C. to 150 degrees C.

When the hammer 200 is pushed into the anvil 100 to close the tube 30, interaction between the face wall 222 and the stop wall 140 may limit translation of the hammer 200 into the slot 120. In some embodiments, the arms 230 may extend into the sleeves 124 beyond the stop wall 140. Once in the closed position, engagement of the stop surface 236 with the second detents 136 prevent separation of the anvil 100 and the hammer 200 such that the clamp 10 prevents flow of fluid through the lumen 34 of the tube 30. In the closed position, the clamp 10 may be longitudinally fixed relative to the tube 30. In certain embodiments, in the closed position, the clamp 10 may be capable of sliding longitudinally along the tube 30 while remaining in the closed position.

In some situations, it may be desired to release the clamp 10 from the closed position such that the clamp 10 returns to the open position to allow fluid to flow through the tube 30 or to reposition the clamp 10 along the tube 30. In some embodiments, the clamp 10 can be released to the closed position and reused on another tube 30. To release the clamp 30, a tool (not shown) may be passed through the second sidewall 114 into one or both of the sleeves 124 to release the arms 230 of the hammer 200 from the closed detent 136. The tool may engage the leading surface 234 of the arms 230 to urge the arms 230 inward until the stop surface 236 is moved inward beyond the closed detent 136 such that the hammer 200 is free to withdraw from within the slot 120 of the anvil 100. The tool may be used to retract or push the hammer 200 out of the slot 120, e.g., towards the first sidewall 112. Additionally or alternatively, engagement of the wall 32 with the stop wall 140 and the face wall 222 may urge or push the hammer 200 out of the slot 120 to return the hammer 200 to the open position. The tool may be a single prong tool and inserted into each sleeve 124 individually or may be a dual prong tool and inserted into both sleeves simultaneously. The tool may include engagement surfaces that are angled to complement the leading surfaces 234 of the arms to engage and move the arms 234 inward.

Figure 9:
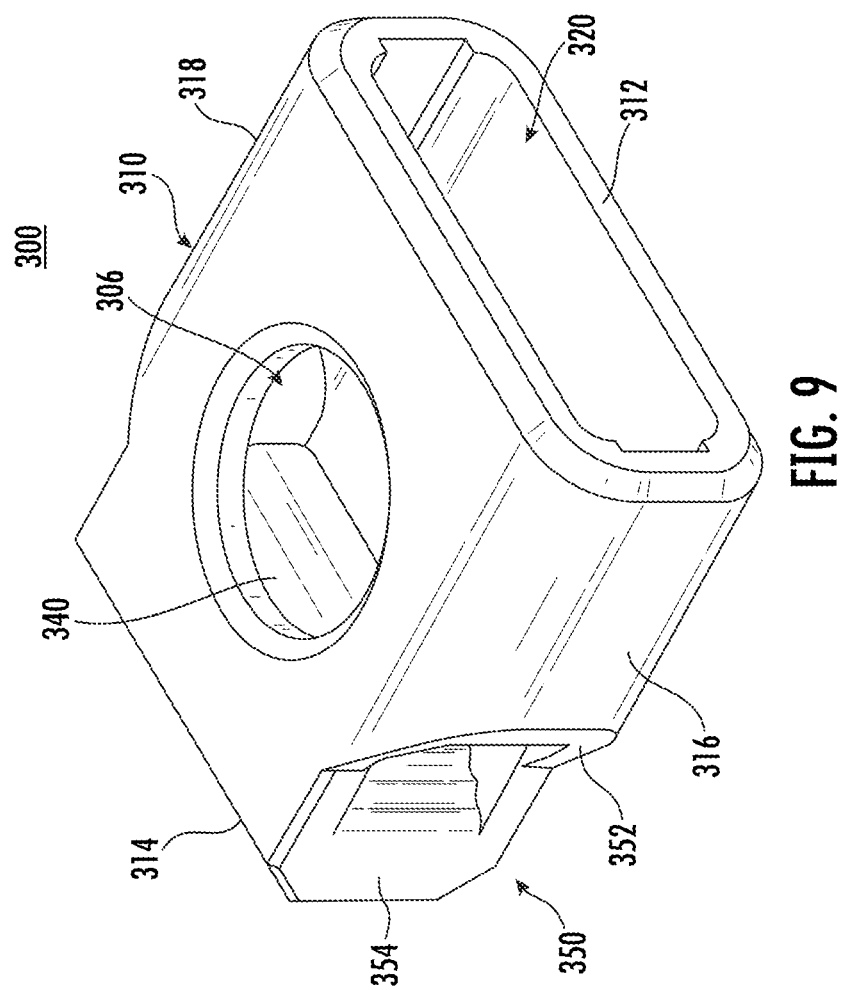
FIG. 9 is a perspective view of another anvil provided in accordance with an embodiment of the present disclosure.
Figure 10:
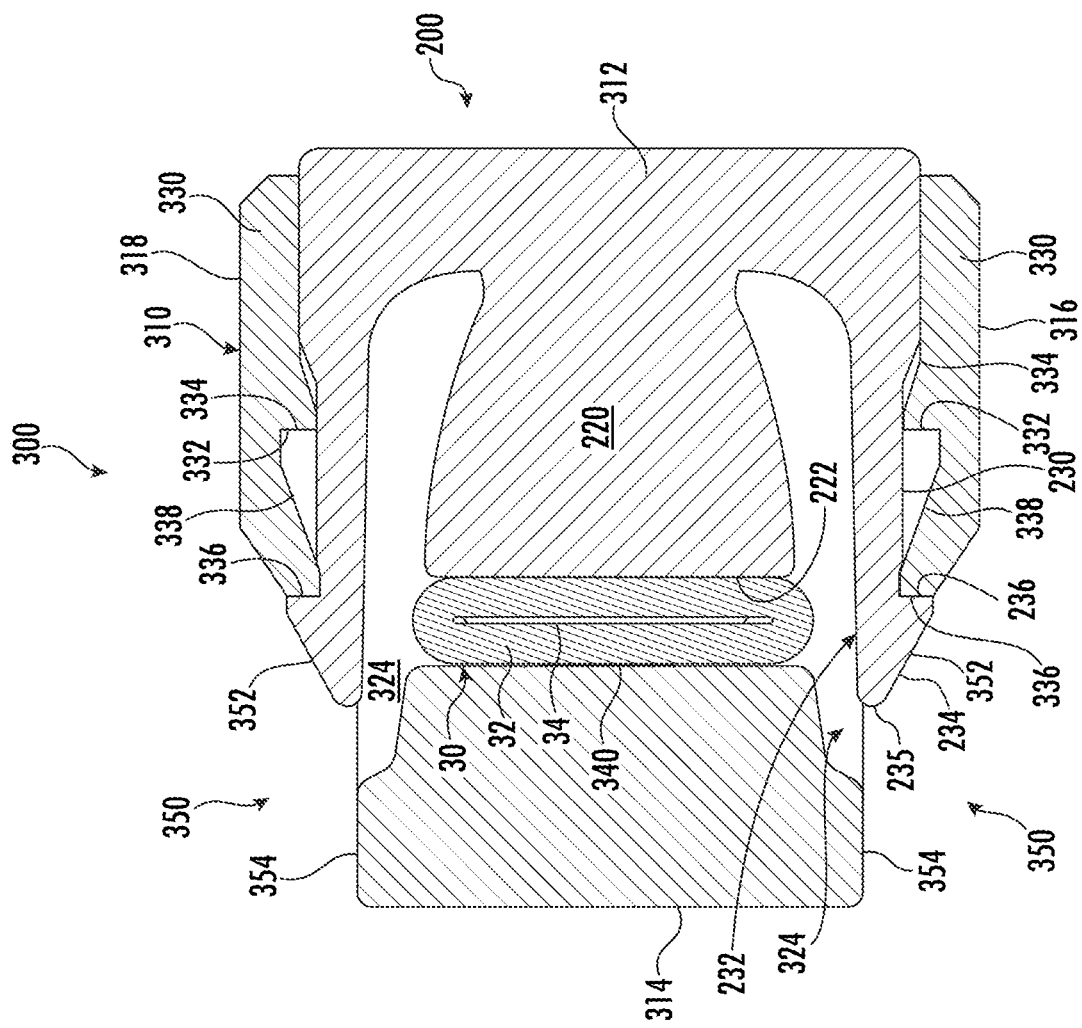
FIG. 10 is a cross-sectional view of a clamp provided in accordance with an embodiment of the present disclosure including the anvil of FIG. 9 with the hammer of FIG. 6 in the closed position to close a tube received through the clamp.

Referring now to FIGS. 9 and 10, another anvil 300 is disclosed in accordance with the present disclosure. The anvil 300 is similar to the anvil 100 detailed above, as such only the differences will be detailed herein for brevity. The anvil 300 may allow for release of the hammer 200 from the closed position to the open position without a tool. For example, the fingers 232 of the hammer 200 may be exposed in the closed position such that the fingers 232 are engageable by fingers or digits of a user as detailed below. As detailed herein, like elements of anvil 300 are labeled in a similar manner to anvil 100 with a leading "3" in place of the leading "1". For example, the anvil 300 has a body 310 which is similar to the body 110 of the anvil 100.

With particular reference to FIG. 10, the anvil 300 includes cutouts 350 in the third sidewall 316 and the fourth sidewall 318 adjacent the second sidewall 314. The cutouts 350 provide access to the sleeves 324 such that when the anvil 200 is in the closed position, the fingers 232 of the arms 230 are accessible such that the anvil 200 can be released by pressing the fingers 232 towards one another without the need for a tool. For example, the fingers 232 may be pressed towards one another by two digits of a user. When the fingers 232 are pressed towards one another such that the lock surface 236 are inboard of the closed detents 336 of the racks 330, the hammer 200 may be urged towards the open position. Specifically, the force on the fingers 232 of the hammer 200 may be on the leading surfaces 234 such that as the fingers 232 are urged inwards, the force also urges the hammer 200 towards the open position. Additionally or alternatively, the tube 30, being compressed in the closed position, may urge the hammer 200 towards the open position when the fingers 232 are inboard of the closed detents 136.

The cutouts 350 are substantially similar to one another, as such, only the cutout 350 defined in the third sidewall 316 will be detailed herein. The cutout 350 is a notch removed from a portion of the body 310. The cutout 350 is defined by a first cutout wall 352 and a second cutout wall 354. The first cutout wall 352 extends from the third sidewall 316 towards the fourth sidewall 318. As shown, the third sidewall 316 extends from the third sidewall 316 towards the fourth sidewall 318 and the second sidewall 314. The first cutout wall 352 may extend from the third sidewall 316 at an angle similar to the angle of the ramps 334, 338. In some embodiments, the first cutout wall 352 may extend orthogonally from the third sidewall 316, e.g., on a plane parallel to the first and second sidewalls 312, 314. As shown, the second cutout wall 354 extends orthogonally from the second sidewall 314 towards the first sidewall 312 in a plane parallel to the third and fourth sidewalls 316, 318. The second cutout wall 354 is positioned at a point along the second sidewall 314 to pass through the sleeve 324. In some embodiments, the second cutout wall 354 may extend from the second sidewall 314 at an angle that is not orthogonal to the second sidewall 314. The first and second cutout walls 352, 354 intersect one another at a positioned between the closed detent 336 and the second sidewall 314 such that a portion of the finger 232 of the hammer 200 is accessible through the cutout 350 when the hammer 200 is in the closed position.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A clamp for closing a flexible tube, the clamp comprising:
    an anvil including a passage and a slot defined therein, the passage configured to receive a flexible tube therethrough, the anvil comprising a first rack and a second rack opposing one another, the first rack and the second rack each defining a portion of the slot, the first rack and the second rack each including a first detent and a second detent; and
    a hammer slidably received within the slot of the anvil, the hammer securable in a first position in the slot of the anvil in which the passage of the anvil is substantially unoccluded and a second position in which the passage of the anvil is occluded, the hammer and the anvil configured to prevent fluid from flowing through a flexible tube received in the passage when the hammer is in the second position, the hammer disposed substantially within the anvil in the second position, the hammer comprising:
    a head; and
    a pair of arms spaced apart by the head, each arm having a finger, each finger having a lock surface, the lock surface of each finger engaged with a respective one of the first detents in the first position and a respective one of the second detents in the second position.

2. The clamp according to claim 1, wherein the anvil includes a cutout defined adjacent the second detent, the cutout providing access to the finger such that the finger is capable of being released from the second detent by a digit of a user.

3. The clamp according to claim 1, wherein the anvil and the hammer are configured to function when cryogenically frozen.

4. The clamp according to claim 1, wherein the hammer is removable from the slot.

5. The clamp according to claim 1, wherein the hammer is formed separate from the anvil.

6. A clamp comprising:
    an anvil including a passage and a slot defined therein, the passage and the slot orthogonal to one another, the passage configured to receive a flexible tube therethrough, the anvil including a pair of ramps extending into the slot, the pair of ramps opposing one another with the slot defined therebetween; and
    a hammer slidably received within the slot, the hammer having a pair of arms and a head positioned between the pair of arms, the hammer securable in a first position in the slot of the anvil in which the head is disposed outside of the passage and a second position in which the head is disposed within the passage, the head configured to cooperate with the anvil to prevent a fluid from flowing through the flexible tube in the second position, the hammer substantially within the anvil when in the second position, each arm of the pair of arms including a leading surface, the leading surface of each arm engaged with a respective of ramp the pair of ramps between the first position and the second position such that the engagement of the leading surface and the respective ramp urges the hammer towards the first position.

7. The clamp according to claim 6, wherein the anvil includes a rack defined in an interior wall thereof, at least one of the pair of arms configured to ratchet along the rack to secure the hammer in the first and second positions.

8. The clamp according to claim 7, wherein the anvil includes a notch defined adjacent the rack, the notch configured to expose a portion of the hammer when the hammer is in the second position such that the hammer is capable of being released from the second position by one or more digits of a user.

9. The clamp according to claim 7, wherein the hammer is removable from the slot.

10. The clamp according to claim 6, wherein the hammer is formed separate from the anvil.

11. A clamp for closing a flexible tube, the clamp comprising:
    an anvil including a passage and a slot defined therein, the passage configured to receive a flexible tube therethrough, the anvil comprising:
    a first rack and a second rack opposing one another with the slot defined therebetween, the first rack and the second rack each including a first ramp and a second ramp, the first ramp and the second ramp of the first rack extending into the slot toward the second rack and the first ramp and the second ramp of the second rack extending into the slot toward the first rack; and a hammer slidably received within the slot of the anvil, the hammer securable in a first position in the slot of the anvil in which the passage of the anvil is substantially unoccluded and a second position in which the passage of the anvil is occluded, the hammer and the anvil configured to prevent fluid from flowing through a flexible tube received in the passage when the hammer is in the second position, engagement of the hammer with the first rack and the second rack of the anvil configured to maintain the anvil in the first position or in the second position, the hammer comprising a pair of arms, each arm having a leading surface, the leading surfaces angled to work in concert with the first ramps to urge the hammer in a first direction away from the anvil and to work in concert with the second ramps to urge the hammer in the first direction and towards the first position.

12. The clamp according to claim 11, wherein the hammer is formed separate from the anvil.

* * * * *